US007067671B2

(12) United States Patent
Zhong et al.

(10) Patent No.: US 7,067,671 B2
(45) Date of Patent: Jun. 27, 2006

(54) PROCESS FOR THE PREPARATION OF TETRASUBSTITUTED IMIDAZOLE DERIVATIVES AND NOVEL CRYSTALLINE STRUCTURES THEREOF

(75) Inventors: Hua Zhong, Lansdale, PA (US); Silke Dubberke, Floershein (DE); Stefan Müller, Zurich (CH); Armin Rossler, Schaffhausen (CH); Thomas W. Schultz, Richboro, PA (US); Daniel J. Korey, Yardley, PA (US); Thomas Otten, Zurich (CH); Donald G. Walker, Pipersville, PA (US); Ahmed Abdel-Magid, Ambler, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 306 days.

(21) Appl. No.: 10/081,553

(22) Filed: Feb. 22, 2002

(65) Prior Publication Data

US 2003/0045723 A1    Mar. 6, 2003

Related U.S. Application Data

(60) Provisional application No. 60/278,607, filed on Mar. 26, 2001.

(51) Int. Cl.
*C07D 401/04* (2006.01)
(52) U.S. Cl. .................................. 546/274.1; 546/210
(58) Field of Classification Search ................. 546/210, 546/274.1
See application file for complete search history.

(56) References Cited

U.S. PATENT DOCUMENTS

| 5,648,373 A | 7/1997 | Winkler et al. |
| 5,670,527 A | 9/1997 | Adams et al. |
| 5,965,583 A | 10/1999 | Beers et al. |

FOREIGN PATENT DOCUMENTS

| DE | 10 10.969 B | 6/1957 |
| DE | 29 50 478 A | 6/1981 |
| DE | 35 04 677 A | 8/1986 |
| WO | WO 96/21452 A1 | 7/1996 |
| WO | WO 98/47892 A1 | 10/1998 |
| WO | WO 99/31089 A | 6/1999 |

OTHER PUBLICATIONS

Sakamoto et al.: "Palladium-catalyzed cross-coupling reaction of haloazoles with phenylsulfonylacetonirile", Synthesis, George Thieme Verlag. Stuttgart, De, No. 6, Jun. 1992, pp. 552-554, XP002175324..

V.V. Golovko et al: "Nitrosochlorination Reaction of substituted imidazol-2-ones" Chemistry of Heterocyclic Compounds, vol. 22, No. 10, 1986 XP001099099.

Chemical Abstracts: vol. 54, No. 14, Jul. 25, 1960, Columbus, Ohio, US Abstract No. 14224i, Ryozo Motoyama et al.: "Thiophene compounds. XII. On the fluorescence of thiophene compounds" XP002205325 & Nippon Kagaku Zasshi, vol. 78, 1957, pp. 965-969 Abstract.

Katritzky, Alan R. et al. "Stabilization of carbanionic centers by neutral N-heterocyclic rings" J. Chem. Res., Synop. 1982, (2) 26-7 Coden: JRPSDC;ISSN: 0308-2342, XP001083860.

Kim, Yong Boon et al: "Condensation reactions of aryl acyloins with ureas in ethylene glycol" J. Heterocycl. Chem. (1994) 31(6), 1653-6, XP001083903.

(Continued)

*Primary Examiner*—Patricia L. Morris
(74) *Attorney, Agent, or Firm*—Thomas Dodd

(57) ABSTRACT

The present invention relates to a process for preparing tetrasubstituted imidazole derivatives of the general formula (I)

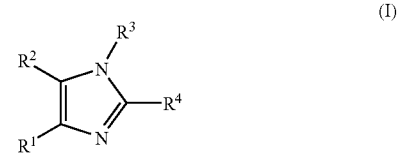

wherein $R^1$, $R^2$, $R^3$ and $R^4$ are as defined in the specification below.

The present invention further relates to a process for preparing the compound of formula (II)

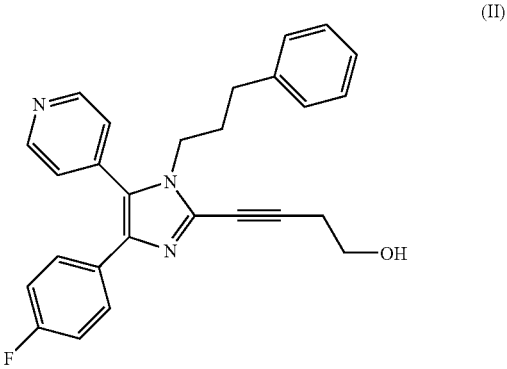

and novel crystalline structures of the compound of formula (II).

3 Claims, No Drawings

OTHER PUBLICATIONS

Purushothaman, E. et al: Regiospecific photochemical transformations of 4, 5-diaryl-DELTA.4-imidazolin-2-ones: ketal formation and cyclodehydrogenation: Proc—Indian Acad. Sci., Chem. Sci. 1989 XP001083539 101(5) p. 391-399.

Feng, Jun-Cai et al: "Condensation reaction of acyloins with urea without solvent under microwave irradiation" Organic preparations and procedures International 1997, 29(6), 687-688, XP001083871.

Mloston, Grzwgorz et al: "Synthesis of imidazole derivatives using 2-unsubstituted 1H-imidazole 3-oxides" Helvetica Chimica Acta (2000), 83(4) 728-738 XP001083538.

Antolini, Marinella et al: "Analogs of 4, 5-bis(3,5-dichlorophenyl)-2-trifluoromethyl-1H-imidazole as potential antibacterial agents" Bioorganic & Medicinal Chemistry Letters 1999, 1023-1028 XP004162577.

Greenberg, H. et al.: "Action of bromine in acetic acid on 4, 5-diphenyl-2, imidazolone" J. Org. Chem. 1966, 31(12), 3951-4 XP001088269.

Sheldrake, P.W., *The Anion of 4-Dimethoxymethylpyridine, A Convenient Synthesis of some 4-pyridyl Ketones*, Synthetic Communications, 23(14), 1993, p. 1967-1971.

Ojima, I. et al., *Syntheses of New Fluorine-Containing Taxoids by Means of β-lactam Synthon Method, Tetrahedron*, vol. 52, No. 1, 1996, p. 209-224.

PROCESS FOR THE PREPARATION OF TETRASUBSTITUTED IMIDAZOLE DERIVATIVES AND NOVEL CRYSTALLINE STRUCTURES THEREOF

CROSS REFERENCE TO RELATED APPLICATION

This application claims priority from U.S. provisional application Ser. No. 60/278,607, filed Mar. 26, 2001, the contents of which are hereby incorporated by reference.

FIELD OF THE INVENTION

The present invention relates to a process for preparing tetrasubstituted imidazole derivatives of the general formula (I)

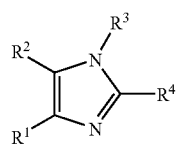

wherein $R^1$, $R^2$, $R^3$ and $R^4$ are as defined in the specification below.

The present invention further relates to a process for preparing the compound of formula (II)

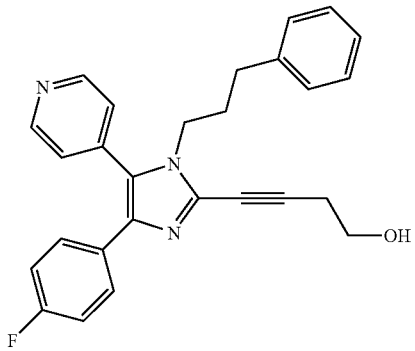

and novel crystalline structures of the compound of formula (II).

BACKGROUND OF THE INVENTION

The invention relates to a process for preparing tetrasubstituted imidazole derivatives represented by the formula (I)

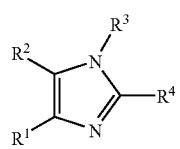

wherein $R^1$, $R^2$, $R^3$ and $R^4$ are as defined in the specification below.

The compounds of formula (I) inhibit the in vitro activity of p38 in the nanomolar range. In addition, the compounds inhibit the in vitro secretion of tumor necrosis factor α (TNF-α) and IL-β in the nanomolar range. Animal models demonstrate the inhibition of LPS induces TNF-α, as well as the inhibition of rheumatoid arthritis. The compounds of formula (I) are useful in the treatment of a variety of cytokine related disorders including rheumatoid arthritis, inflammatory bowel disease, septic shock, osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, acute pancreatitis, allograft rejection, allergic inflammation in the lung, atherosclerosis, multiple sclerosis, cachexia, Alzheimer's disease, stroke, Crohn's disease, ischemia, congestive heart failure, pulmonary fibrosis, hepatitis, glioblastoma, Guillain-Barre Syndrome and systemic lupus erythematosus. (U.S. Pat. No. 5,965,583 Issued Oct. 12, 1999)

The current invention relates to an efficient process for preparing compounds of formula (I). In a further aspect, the present invention relates to a process for preparing the compound of formula (II).

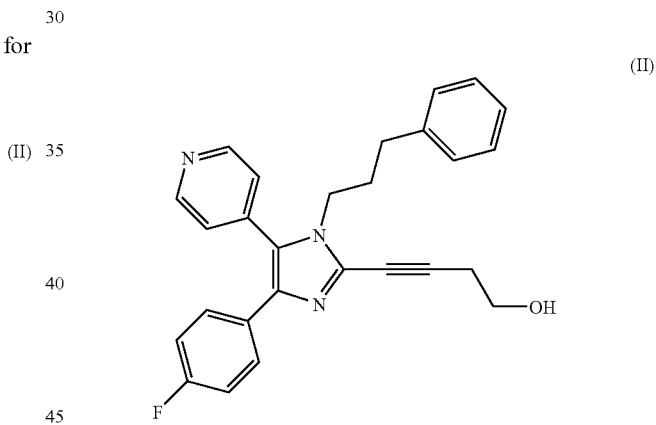

The compound of formula (II) is an orally active inhibitor of p38 kinase. p38 kinase inhibitors have utility in suppressing the release of TNF-α from monocytes and would be expected to suppress signal transduction initiated by this proinflammatory mediator. Thus p38 kinase inhibitors have utility in the treatment of various inflammatory and autoimmune disorders such as rheumatoid arthritis, sepsis, inflammatory bowel disease, acute respiratory distress syndrome, as well as cachexia and bone resorption (osteoporosis and osteoarthritis).

The present invention further relates to novel crystalline structures of the compound of formula (II), more specifically Form A and Form B.

A process for synthesizing pyridyl imidazole compounds is disclosed in U.S. Pat. No. 5,670,527, issued Sep. 23, 1997 (Adams, J. L., et. al., SmithKline Beecham Corp. Assignee) and in PCT application WO 96/21452, published Jul., 18, 1996 (Adams, J. L., et. al., SmithKline Beecham Corporation).

U.S. Pat. No. 5,965,583 (Issued Oct. 12, 1999), which is incorporated herein by reference, disclose a process for preparing the compounds of formula (I). This process requires chromatographic separation of intermediates, making it unsuitable for large scale production.

Thus there exists a need for a process which is compatible with large scale production needs and which achieves acceptable levels of purity and yield.

BRIEF SUMMARY OF THE INVENTION

The invention relates to a process for preparing a compound of formula (I):

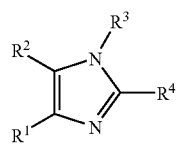

wherein
$R^1$ is selected from the group consisting of phenyl, substituted phenyl, (where the substituents are selected from $C_1$–$C_5$alkyl, halogen or trifluoromethyl) and heteroaryl, where the heteroaryl contains 5 to 6 ring atoms;
$R^2$ is selected from the group consisting of phenyl, substituted phenyl, (where the substituents are selected from $C_1$–$C_5$alkyl, halogen or trifluoromethyl) and heteroaryl, where the heteroaryl contains 5 to 6 ring atoms and is optionally $C_1$–$C_4$alkyl substituted;
$R^3$ is selected from the group consisting of hydrogen, aryl$C_1$–$C_5$alkyl, substituted aryl$C_1$–$C_5$alkyl, (where the aryl substituents are independently selected from one or more of $C_1$–$C_5$alkyl, $C_1$–$C_5$alkoxy, halogen, amino, $C_1$–$C_5$alkylamino or di($C_1$–$C_5$alkyl)amino), phthalimido$C_1$–$C_5$alkyl, succinimido$C_1$–$C_5$alkyl, $C_1$–$C_5$alkylcarbonyl$C_1$–$C_5$alkyl, aryloxycarbonyl$C_1$–$C_5$alkyl, and heteroaryl$C_1$–$C_5$akyl, where the heteroaryl contains 5 to 6 ring atoms;
$R^4$ is

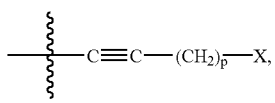

where
p is an integer from 0 to 9;
X is selected from the group consisting of hydrogen, hydroxy, vinyl, substituted vinyl, (where one or more substituents are selected from fluorine or chlorine), ethynyl, substituted ethynyl (where the substituent is selected from fluorine or chlorine), $C_1$–$C_5$alkyl, substituted $C_1$–$C_5$alkyl (where the alkyl substituents are selected from one or more of $C_1$–$C_5$alkoxy, trihaloalkyl, phthalamido or amino), $C_3$–$C_7$cycloalkyl, $C_1$–$C_5$alkoxy, substituted $C_1$–$C_5$alkoxy (where the alkyl substituents are selected from phthalimido or amino), phthalimidooxy, phenoxy, substituted phenoxy (where the phenyl substituents are selected from $C_1$–$C_5$alkyl, fluorine, chlorine or $C_1$–$C_5$alkoxy), phenyl, substituted phenyl (where the phenyl substituents are selected from $C_1$–$C_5$alkyl, fluorine, chlorine or $C_1$–$C_5$alkoxy), aryl$C_1$–$C_5$alkyl, substituted aryl$C_1$–$C_5$alkyl (where the aryl substituents are selected from $C_1$–$C_5$alkyl, fluorine, chlorine or $C_1$–$C_5$alkoxy), arylhydroxy$C_1$–$C_5$alkylamino, $C_1$–$C_5$alkylamino, di($C_1$–$C_5$alkyl)amino, nitrile, oxime, benzyloxyimino, $C_1$–$C_5$alkyloxyamino, phthalimido, succinimido, $C_1$–$C_5$alkylcarbonyloxy, phenylcarbonyloxy, substituted phenylcarbonyloxy (where the phenyl substituents are selected from $C_1$–$C_5$alkyl, fluorine, chlorine or $C_1$–$C_5$alkoxy), phenyl$C_1$–$C_5$alkylcarbonyloxy, (where the phenyl substituents are selected from $C_1$–$C_5$alkyl, fluorine, chlorine or $C_1$–$C_5$alkoxy), aminocarbonyloxy, $C_1$–$C_5$alkylaminocarbonyloxy, di($C_1$–$C_5$alkyl)aminocarbonyloxy, $C_1$–$C_5$alkoxycarbonyloxy, substituted $C_1$–$C_5$alkoxycarbonyloxy (where the alkyl substituents are selected from the group consisting of methyl, ethyl, isopropyl and hexyl), phenoxycarbonyloxy, substituted phenoxycarbonyloxy (where the phenyl substituents are selected from $C_1$–$C_5$alkyl, fluorine, chlorine or $C_1$–$C_5$alkoxy), $C_1$–$C_5$alkylthio, substituted $C_1$–$C_5$alkylthio (where the alkyl substituents are selected from hydroxy and phthalimido), $C_1$–$C_5$alkylsulfonyl, phenylsulfonyl and substituted phenylsulfonyl (where the phenyl substituents are selected from fluorine, chlorine, $C_1$–$C_5$alkoxy or trifluoromethyl);
or pharmaceutically acceptable salts thereof;
comprising

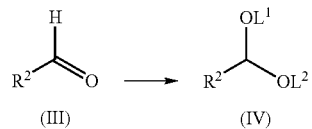

reacting an aldehyde of formula (III) to produce the corresponding compound of formula (IV), where $L^1$ and $L^2$ are independently selected from the group consisting of $C_1$–$C_4$alkyl and $C_1$–$C_4$aralkyl; or $L^1$ together with $L^2$ is selected from the group consisting of —CH$_2$—CH$_2$— (optionally substituted with one to four $C_1$–$C_3$ alkyl), and —CH$_2$—CH$_2$—CH$_2$— (optionally substituted with one to six $C_1$–$C_3$ alkyl);

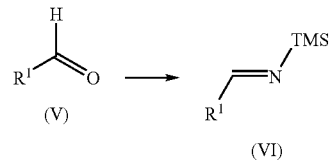

in a separate reaction vessel, reacting an aldehyde of formula (V), with an alkali metal salt of bis(trimethylsilyl) amide, to produce the corresponding trimethylsilyl substituted imine of formula (VI);

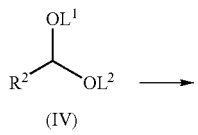

-continued

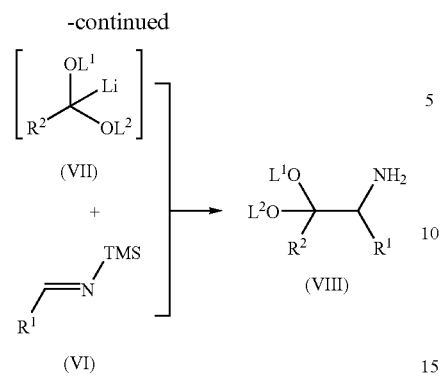

reacting the compound of formula (IV) with an alkyl lithium to produce the corresponding lithium intermediate of formula (VII);

reacting the lithium intermediate of formula (VII) with the trimethylsilyl substituted imine of formula (VI) to produce the corresponding compound of formula (VIII);

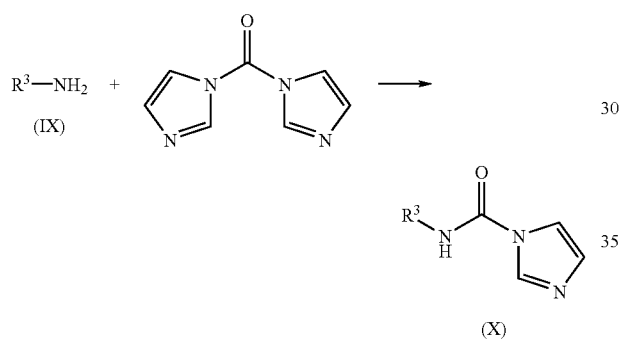

in a separate vessel, reacting a substituted amine of formula (IX) with N,N'-carbonyldiimidazole, to yield the corresponding compound of formula (X);

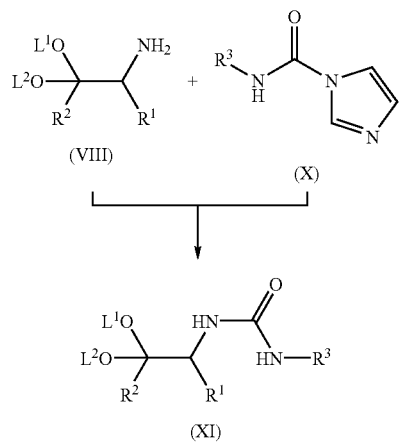

reacting the compound of formula (VIII) with the compound of formula (X), to produce the corresponding compound of formula (XI);

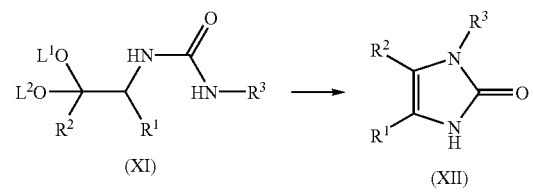

cyclizing the compound of formula (XI), under acid conditions of pH less than about 7, to produce the corresponding compound of formula (XII);

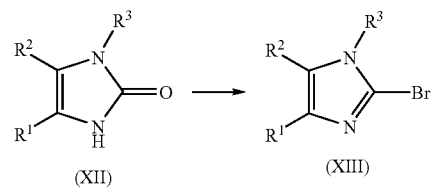

reacting the compound of formula (XII) with $POBr_3$, $PBr_5$, or in a mixture of $PBr_3$ and $Br_2$, to yield the corresponding compound of formula (XIII);

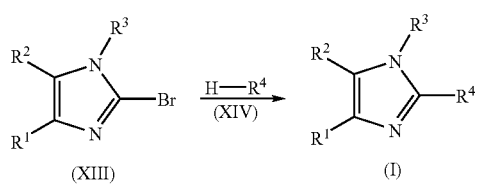

displacing the bromine on the compound of formula (XIII) by reacting with a compound of formula (XIV), to produce the corresponding compound of formula (I).

In another aspect, the present invention relates to a process for preparing the compound of formula (II).

In a further aspect, the present invention is directed to intermediates of formula (XI) and formula (XII), and a process for preparing same. In still another aspect of the present invention is a process for preparing the intermediate compound of formula (XIII).

In a further aspect, the present invention is directed to novel crystalline structures of the compound of formula (II), wherein the crystalline forms are herein referred to as Form A and Form B, which may be characterized by their respective X-ray powder diffraction patterns.

DETAILED DESCRIPTION OF THE INVENTION

As used herein, the term "alkyl" whether used alone or as part of a substituent group, includes straight, branched and cyclic chain alkyl groups. For example, alkyl groups include methyl, ethyl, propyl, isopropyl, butyl, isobutyl, sec-butyl, t-butyl, pentyl, cyclopropyl, cyclobutyl, cyclopentyl, cyclohexyl, and the like.

As used herein, unless otherwise noted, "alkoxy" shall denote a group of the formula —O-(alkyl), for example, methoxy, ethoxy, n-propoxy, sec-butoxy, t-butoxy, n-hexyloxy and the like.

As used herein, unless otherwise noted, "aryl" shall refer to unsubstituted mono and fused aromatic rings such as phenyl, naphthyl, and the like.

As used herein, unless otherwise noted, "heteroaryl" shall denote any five or six membered monocyclic aromatic ring structure containing at least one heteroatom selected from sulfur, oxygen and nitrogen. In the case of five-membered rings, the heteroaryl will contain one sulfur, oxygen or nitrogen atoms and, in addition, may contain up to three additional nitrogen atoms. In the case of six-membered rings, the heteroaryl may contain up to three nitrogen atoms. Examples of such heteroaryls include, but are not limited to, pyridin-2-yl, pyridin-3-yl, pyridin-4-yl, pyrimidi-3-yl, furan-2-yl, furan-3-yl, thiophen-2-yl, thiophen-3-yl, pyridazinyl, triazinyl, thiazolyl, oxazolyl, pyrazolyl, and the like.

As used herein, unless otherwise noted, "aralkyl" shall mean any $C_1$–$C_5$ alkyl group substituted with an aryl group such as phenyl, naphthyl and the like. For example, benzyl, phenylethyl, and the like.

As used herein, unless otherwise noted, "halogen" shall mean chlorine, bromine, fluorine and iodine.

As used herein, the term "alkali metal" shall refer to a Group I metal cation such as lithium, sodium, potassium and cesium cations.

With reference to substituents, the term "independently" means that when more than one of such substituents is possible, such substituents may be the same or different from each other.

During any of the processes of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The invention relates to a process for preparing compounds of formula (I) as more fully described in Scheme 1.

SCHEME 1

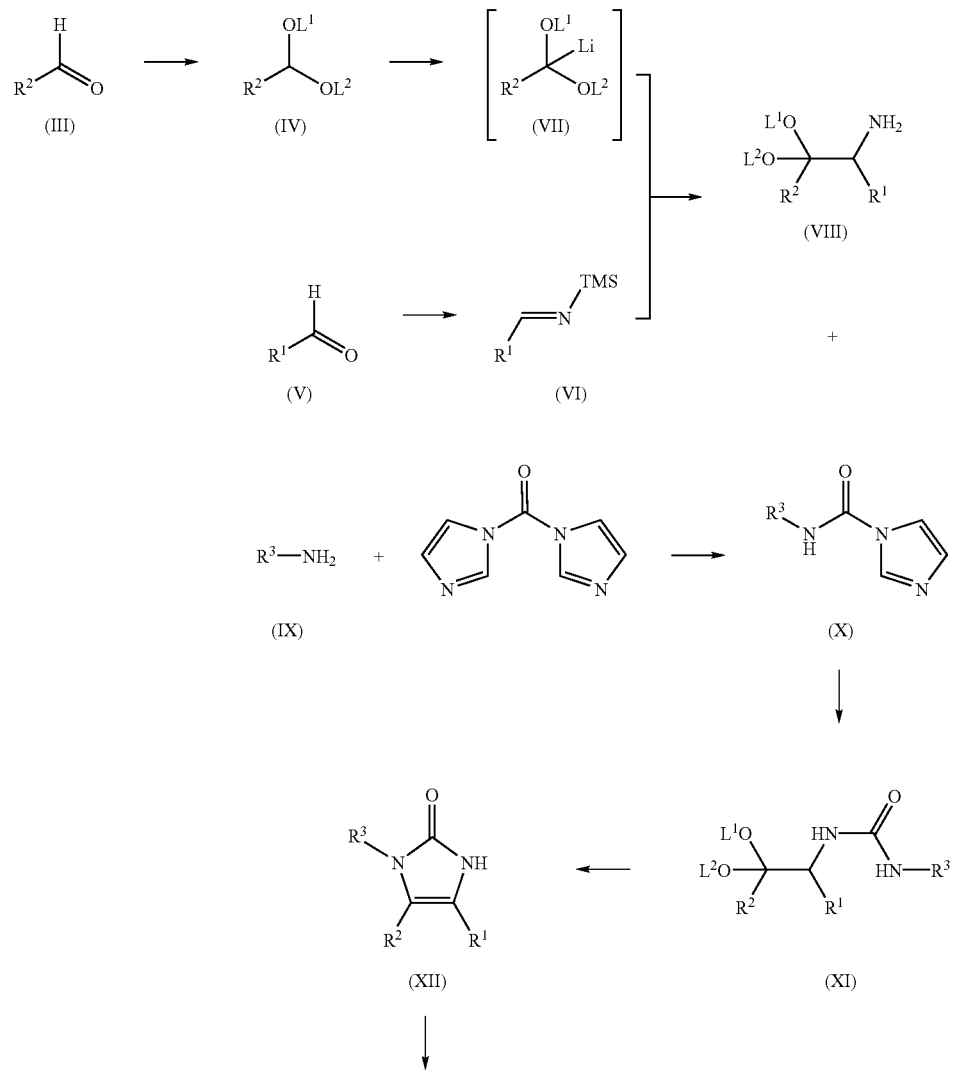

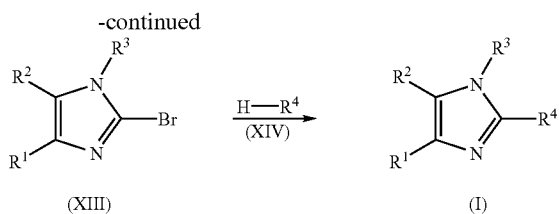

As set forth in Scheme 1 above, an aldehyde of formula (III), a known compound or compound prepared by known methods, is reacted with an alcohol, diol or tri-alkoxymethane, preferably trimethoxymethane, preferably in the presence of methanol, in a solvent capable of azeotropic removal of water such as benzene, toluene, xylene, and the like, in the presence of an acid such as sulfuric acid, p-toluenesulfonic acid, and the like, preferably sulfuric acid, at reflux temperature, to produce the corresponding compound of formula (IV). (Sheldrake, P. W., *Synth Commun.* (1993) 23(14), 1967–71)

In a separate reaction vessel, an aldehyde of formula (V), a known compound or compound prepared by known methods, is reacted with an alkali metal salt of bis(trimethylsilyl) amide, preferably lithium bis(trimethylsilyl)amide, in an organic solvent such as tetrahydrofuran (THF), diethyl ether, t-butylmethylether (MTBE), and the like, preferably THF, at a temperature in the range of about −20° C. to about room temperature, preferably at a temperature of about 0° C., to produce the corresponding trimethylsilyl (TMS) substituted imine of formula (VI). (Ojima, I., et. al., *Tetrahedron* (1996), 52, 209–224)

The compound of formula (IV) is reacted with an alkyl lithium such as methyl lithium, ethyl lithium, n-butyl lithium, and the like, preferably n-butyl lithium, at a temperature which prevents decomposition of the lithium intermediate of formula (VII), preferably at a temperature of less than or equal to about −20° C., in an organic solvent such as tetrahydrofuran (THF), diethylether, t-butylmethylether (MTBE), and the like, preferably THF, to produce the corresponding lithium intermediate of formula (VII).

The lithium intermediate of formula (VII) is reacted with the TMS substituted imine of formula (VI) in the presence of an organic solvent such as tetrahydrofuran (THF), diethylether, t-butylmethylether (MTBE), and the like, preferably THF, preferably allowing warming of the reaction mixture to about room temperature, to produce the corresponding compound of formula (VIII).

In a separate reaction vessel, a substituted amine of formula (IX), a known compound or compound prepared by known methods, is reacted with N,N'-carbonyldiimidazole, a known compound, in an inert organic solvent, such as tetrahydrofuran (THF), diethylether, t-butylmethylether (MTBE), toluene, dichloromethane (DCM), and the like, preferably THF, preferably at room temperature, to produce the corresponding compound of formula (X).

The compound of formula (VIII) is reacted with the compound of formula (X), in an organic solvent such as toluene, tetrahydrofuran (THF), dimethylformamide (DMF), and the like, preferably toluene, at a temperature in the range of about 50–150° C., preferably for toluene, at about reflux temperature, to produce the corresponding compound of formula (XI).

The compound of formula (XI) is cyclized in an acid such as formic acid, aqueous hydrochloric acid, and the like, preferably aqueous hydrochloric acid, preferably at a temperature in the range of about 80–150° C., most preferably at a temperature in the range of about 95–100° C., to yield the corresponding compound of formula (XII).

The compound of formula (XII) is reacted with phosphorus oxybromide ($POBr_3$) or phosphorous pentabromide ($PBr_5$), preferably $POBr_3$, in an amount equal to at least about 5 equivalents, in an inert organic solvent whose boiling point is greater than or equal to about 110° C., such as tetramethylenesulfone, xylene, toluene, and the like, preferably tetramethylenesulfone, preferably in an amount equal to about 2 weight equivalents, at a temperature of greater than or equal to about 110° C., preferably at a temperature of about 130° C., to yield the corresponding compound of formula (XIII).

Alternatively, the compound of formula (XII) is reacted with a mixture of $PBr_3$ and $Br_2$ (which produces $PBr_5$ in situ), wherein the ratio of $PBr_3$ to $Br_2$ is in the range of about 1:2 to about 2:1, preferably the ratio of $PBr_3$ to $Br_2$ is about 1:1; wherein the amount of the $PBr_5$ produced by the mixture of $PBr_3$ and $Br_2$ is in the range of about 3–3.5 equivalents; in a solvent such as $POCl_3$ or in an inert organic solvent whose boiling point is greater than or equal to about 110° C., such as tetramethylenesulfone (sulfolane), xylene, toluene, and the like, preferably $POCl_3$; at a temperature in the range of about 10–45° C., preferably at a temperature in the range of about 20–35° C.; to yield the corresponding compound of formula (XIII).

The bromine on the compound of formula (XIII) is displaced by reacting with a compound of formula (XIV), a known compound or compound prepared by known methods, in the presence of a Pd(II) catalyst such as diacetoxybis (triphenylphosphine) palladium ($Pd(OAc)_2(Ph_3P)_2$,), dichloro bis(triphenylphosphine) palladium ($PdCl_2(Ph_3P)_2$), and the like, or in the presence of a catalyst such as palladium acetate ($Pd(OAc)_2$) or palladium chloride ($PdCl_2$), wherein the palladium acetate or palladium chloride catalyst is further in the presence of triphenylphosphine, preferably the catalyst is diacetoxybis (triphenylphosphine) palladium, preferably in the presence of a co-catalyst such as copper(I) iodide (CuI), Fe powder, and the like, preferably CuI, in the presence of an organic amine such as diisopropylamine, diisopropylethylamine (DIPEA), triethylamine (TEA), piperidine, and the like, or an inorganic base such as $K_2CO_3$, $Cs_2CO_3$, and the like, preferably an organic amine, more preferably diisopropylamine, optionally in an inert organic solvent such as THF, t-butyl methyl ether (MTBE), diethyl ether, DMF, acetonitrile, and the like, with heating to a temperature in the range of about 60–100° C., preferably to a temperature of about 75° C., to produce the corresponding compound of formula (I).

Alternatively, the compound of formula (XI) may be prepared according to the process outlined in Scheme 2

SCHEME 2

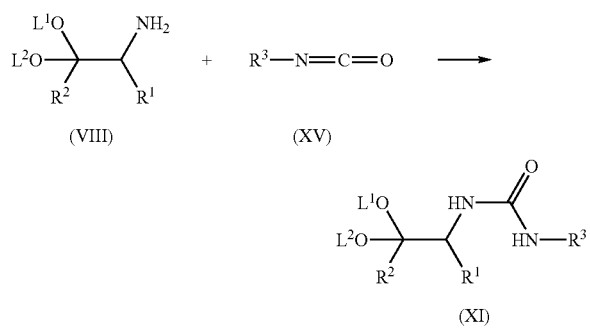

wherein $L^1$, $L^2$, $R^1$, $R^2$ and $R^3$ are as set forth above.

More particularly, the compound of formula (VIII) is reacted with a compound of formula (XV), in an inert organic solvent such as tetrahydrofuran (THF), dimethylformamide (DMF), toluene, and the like, preferably THF, preferably at room temperature, to produce the corresponding compound of formula (XI).

In a preferred embodiment of the invention, the process is used to prepare the compound of formula (II). Preferably, the compound of formula (II) is further purified by known methods such as recrystallization from an organic solvent such as toluene, methanol, acetone, acetonitrile, and the like or from a mixture of organic solvents such as ethyl acetate/hexane, THF/toluene, ethyl acetate/toluene, and the like.

The present invention is further directed to novel crystalline structures of the compound of formula (II). The crystalline forms of the compound of formula (II) may be prepared by recrystallization of the compound of formula (II) from a suitable organic solvent such as acetone, acetonitrile, THF/toluene mixture, and the like.

Recrystallization of the compound of formula (II) as described above will yield one of two novel crystalline forms, herein referred to as Form A and Form B. Form B is obtained by recrystallization from acetone or a mixture of THF:toluene, more preferably a 1:2 mixture of THF:toluene. Form A is obtained by recrystallization from acetonitrile.

The novel crystalline forms of the compound of formula (II) may be characterized by their respective x-ray powder diffraction patterns utilizing a Siemens D5000T-T based powder diffractometer using $CuK_\alpha$ radiation and the following system conditions:

a) $CuK_\alpha$ radiation, 35 mA, 40 KV b) Optics 1 mm slit, Gobel mirrors, 0.6 mm slit, & vertical soller slits between tube and sample LiF monochromator between sample and detector c) Scan 5 to 35°2θ at 0.02 Step Size at a rate of 1°2θ/minute d) TTK-450 variable temperature/humidity stage and holder Form A of the compound of formula (II) may be characterized by its X-ray diffraction pattern, which comprises the major peaks as listed in Table 1.

TABLE 1

FORM A POWDER X-RAY DIFFRACTION PEAKS

| ANGLE 2θ | d-Spacing (Å) | Relative Intensity (%) |
|---|---|---|
| 6.599 | 13.384 | 15.2 |
| 7.817 | 11.300 | 14.4 |
| 11.676 | 7.573 | 33.2 |
| 17.536 | 5.053 | 11.6 |
| 18.428 | 4.811 | 38.3 |
| 19.318 | 4.591 | 19.9 |
| 19.948 | 4.447 | 100.0 |
| 20.852 | 4.256 | 10.1 |
| 21.463 | 4.137 | 43.3 |
| 23.260 | 3.821 | 39.5 |
| 23.883 | 3.723 | 80.6 |
| 24.804 | 3.587 | 57.9 |
| 25.119 | 3.542 | 31.9 |
| 25.579 | 3.480 | 12.3 |
| 26.251 | 3.392 | 21.5 |
| 26.725 | 3.333 | 58.6 |
| 28.229 | 3.159 | 11.4 |
| 30.487 | 2.9296 | 23.0 |
| 31.614 | 2.8278 | 17.6 |

Form B of the compound of formula (II) may be characterized by its X-ray diffraction pattern, which comprises the major peaks as listed in Table 2.

TABLE 2

FORM B POWDER X-RAY DIFFRACTION PEAKS

| ANGLE °2θ | d-Spacing (Å) | Relative Intensity (%) |
|---|---|---|
| 7.206 | 12.257 | 100.0 |
| 8.961 | 9.861 | 14.2 |
| 10.617 | 8.326 | 24.8 |
| 12.438 | 7.110 | 14.0 |
| 15.500 | 5.712 | 33.7 |
| 16.458 | 5.382 | 13.3 |
| 17.360 | 5.104 | 17.2 |
| 17.879 | 4.957 | 37.6 |
| 18.343 | 4.833 | 19.2 |
| 18.665 | 4.750 | 31.8 |
| 19.126 | 4.637 | 16.1 |
| 19.943 | 4.448 | 21.9 |
| 20.491 | 4.331 | 30.8 |
| 21.469 | 4.135 | 52.9 |
| 21.891 | 4.057 | 59.8 |
| 22.371 | 3.971 | 58.7 |
| 22.778 | 3.901 | 12.0 |
| 23.159 | 3.837 | 51.0 |
| 23.870 | 3.725 | 20.8 |
| 24.526 | 3.627 | 15.5 |
| 24.704 | 3.601 | 25.9 |
| 25.113 | 3.543 | 14.7 |
| 26.368 | 3.377 | 11.0 |
| 27.674 | 3.221 | 10.5 |
| 28.088 | 3.174 | 18.3 |
| 28.896 | 3.087 | 21.3 |
| 29.291 | 3.047 | 19.4 |
| 30.201 | 2.9568 | 10.6 |
| 30.501 | 2.9284 | 13.3 |

The following examples describe the invention in greater detail and are intended to illustrate the invention, but not to limit it.

EXAMPLE 1

4-(Dimethoxymethyl)pyridine

To a solution of 4-pyridinecarboxaldehyde (100.00 g, 0.93 mol) and trimethylorthoformate (159.20 g, 1.50 mol) in methanol (180 mL) at 0° C., under $N_2$ was added concentrated sulfuric acid (41 mL, 0.45 mol). The resulting white suspension was heated to reflux and stirred for 24 hours. The reaction solution became clear after 2 h. After cooling to room temperature, the reaction mixture was poured slowly into a solution of 25 wt. % sodium methoxide (360 mL) in methanol (300 mL). The mixture was then concentrated in vacuo to a light brown thick oil. To this crude oil was added t-butylmethyl ether (500 mL), followed by the slow addition of water (40 mL) (to convert the inorganics to filterable solids). After filtration through a pad of Celite, the filtrate was concentrated to yield a light brown oil. The crude oil was vacuum distilled to yield the desired product as a colorless oil Yield: 88.91 g (62.4%)
BP 69–71° C. at 1 mm Hg

EXAMPLE 2

2,2-Dimethoxy-2-(4-pyridyl)-1-(4-fluorophenyl) ethanamine

Step A:
To a stirred solution of 1M lithium bis(trimethylsilyl) amide in THF (300 mL, 0.30 mol), under $N_2$, was added 4-fluorobenzaldehyde (37.23 g, 0.30 mol), dropwise at 0° C. The resulting mixture was stirred at room temperature for 30 min to yield a solution.

Step B:
In a second flask, 4-dimethoxymethylpyridine (38.29 g, 0.25 mol) was mixed with THF (200 mL) and cooled to −20° C. To the solution was slowly added dropwise 2.5M n-butyl lithium in hexane (120 mL, 0.30 mol), with the temperature of the reaction solution maintained between −15 and −20° C. The resulting dark brown reaction mixture was stirred at −20° C. for 15 min. To the reaction mixture was slowly added the solution from step A above. The temperature of the reaction solution was maintained below −15° C. After addition, the dark brown reaction mixture was stirred and warmed up to room temperature. The reaction mixture was quenched with 2N aqueous HCl (500 mL) to a pH of about 2.0, and the resulting layers were separated. The organic layer was extracted once with 1N aqueous HCl (100 mL). The combined aqueous layers were washed with ethyl acetate (2×150 mL) and then basified with addition of 50% aq. NaOH solution, to a pH of about 10. The basified mixture was extracted with ethyl acetate (400 mL, 2×100 mL). The combined ethyl acetate extracts were washed with water (200 mL), brine (200 mL), and dried with $Na_2SO_4$. After concentration in vacuo, the crude product was obtained as a thick brown oil.

Yield: 54.70 g (79%)

EXAMPLE 3

N-(3-phenylpropyl)-1H-imidazole-1-carboxamide

To a suspension of 1,1′-carbonyldiimidazole (33.00 g, 0.203 mol) in THF (100 mL) at room temperature under $N_2$, was added 3-phenylpropylamine (25.00 g, 0.185 mol) in THF (50 mL), dropwise. The reaction mixture became clear during the addition of the 3-phenylpropylamine. After completion of the addition, the clear solution was stirred for 30 min at room temperature and then quenched with water (150 mL) and ethyl acetate (200 mL). The layers were separated and the organic layer washed with water (150 mL), brine (150 mL), and dried with $Na_2SO_4$. The solvents were removed in vacuo to yield a white wax-like solid.

Yield: 47.50 g

EXAMPLE 4

N-(3-phenylpropyl)-N'-[(2.2-dimethoxy-2-(4-pyridyl)-1-(4-fluorophenyl)ethyl)] urea A solution of 2,2-dimethoxy-2-(4-pyridyl)-1-(4fluorophenyl)ethanamine (51.12 g, 0.185 mol) and N-(3-phenylpropyl)-1H-imidazole-1-carboxamide (42.42 g, 0.185 mol) in toluene (300 mL) under $N_2$, was stirred and heated to reflux temperature for 3 h. The solution was cooled to room temperature and the dark brown solution was diluted with ethyl acetate (200 mL). The mixture was washed with water (2×200 mL), brine (200 mL), and dried with $Na_2SO_4$. The solvents were removed in vacuo to yield a brown solid which was recrystallized from a solvent mixture of ethyl acetate/hexane (1:1) to yield an off-white solid.

Yield: 38.00 g (47%)

EXAMPLE 5

1,3-dihydro-1-(3-phenylpropyl)-4-(4-fluorophenyl)-5-(4-pyridyl)-2H-imidazlin-2-One N-(3-phenylpropyl)-N'-[(2,2-dimethoxy-2-(4-pyridyl)-1-(4-fluorophenyl)ethyl)] urea (38.0 g, 86.8 mmol) was dissolved in formic acid (100 mL) to form a brown solution. The solution was heated to 95–100° C. and stirred under $N_2$ for 24 h. The solution was then cooled to room temperature, the formic acid was removed under reduced pressure by rotoevaporator and the residue diluted with ethyl acetate (300 mL). The solution was basified with 6N NaOH to a pH of about 10. An off-white solid formed slowly in the organic layer. The clear aqueous layer was separated and extracted with ethyl acetate (50 mL). The combined organic layers were diluted with t-butylmethylether (350 mL) and stirred for 30 min. The solid product was collected by filtration, washed with t-butylmethyl ether (100 mL) and air-dried for 1 h. The solid product was dried in a vacuum oven at room temperature for 24 h to yield the product as an off-white solid.

Yield: 18.11 g (58%) MP: 198–199.5° C.

EXAMPLE 6

2-bromo-1-(3-phenylpropyl)-4-(4-fluorophenyl)-5-(4-pyridyl)-1H-imidazole HBr salt 1,3-dihydro-1-(3-phenylpropyl)-4-(4-fluorophenyl)-5-(4-pyridyl)-2H-imidazolin-2-one (5.0 g, 13.4 mmol) was suspended in sulfolane (20.0 g,) and treated with $POBr_3$ (19.5 g, 68 mmol). The mixture was heated to 130° C. and stirred under $N_2$ for 3–3.5 h. The reaction solution was cooled to room temperature, diluted with t-butylmethyl ether (100 mL) and cooled further to 0° C. The reaction mixture was quenched slowly with 10% NaOH solution (120 mL) to a pH of about 10. The layers were separated and the aqueous layer was extracted with t-butylmethyl ether (30×2 mL). The combined organic layers were washed with water (50×2 mL), brine (50 mL), and dried with $Na_2SO_4$. The solvent was removed in vacuo and the residue dissolved in a mixture of ethyl acetate (100 mL) and methanol (5 mL). The solution was treated with 2.88M HBr solution in ethyl acetate (9.3 mL, 26.8 mmol). The resulting yellow suspension was warmed on a steam-bath. Methanol (5 mL) was added to the suspension, resulting in the formation of a solution, and the solution was stirred overnight at room temperature (ca. 18 h). Ethyl acetate (50 mL) was then added slowly and the suspension was stirred for another 1 h. The precipitate was collected by filtration and washed with ethyl acetate (50 mL). The solid was dried in a vacuum oven at room temperature for 2 h, to yield the product as a yellowish solid.

Yield: 5.01 g (62%), MP: 214–216° C., (color change at 205° C.)

EXAMPLE 7

4-(4-fluorophenyl)-2-(4-hydroxy-1-butynyl)-1-(3-phenylpropyl)-5-(4-pyridyl)imidazole To a stirred solution of 4-(4-fluorophenyl)-2-iodo-1-(3-phenylpropyl)-5-(4-pyridyl)imidazole (1.42 g, 2.74 mmol) and 3-butyn-1-ol (0.289 g, 4.1 mmol) in diisopropylamine (10 mL) was added bis(acetato)-bis(triphenylphosphine) palladium (0.102 g, 0.14 mmol), followed by the addition of copper(I) iodide (0.052 g, 0.274 mmol). The mixture was stirred at 75° C. for 4 h. The reaction mixture was then cooled to room temperature and quenched with water (100 mL). The mixture was extracted with ethyl acetate (2×50 mL). The combined ethyl acetate extract was washed with water (2×30 mL), brine (30 mL), and dried with $Na_2SO_4$. After removal of solvents, the crude product was obtained as a brown solid.

The crude product was purified by recrystallization from a mixture of ethyl acetate/hexane to yield the product as a yellow solid.

Yield: 0.88 g (75%) MP: 121–122° C.

EXAMPLE 8

1,3-dihydro-1-(3-phenylpropyl)-4-(4-fluorophenyl)-5-(4-pyridyl)-2H-imidazol-2-one N-(3-phenylpropyl)-N'-[(2,2-dimethoxy-2-(4-pyridyl)-1-(4-fluorophenyl)ethyl)] urea (224 g, 0.45 mol) was mixed with 4N HCl (800 g) and heated under reflux for 4–5 h (95–100° C.). Upon completion, the reaction was cooled to room temperature and adjusted to pH 13 with 8N NaOH solution (480 g), resulting in precipitation of a solid product. The pH of the suspension was controlled to pH≧13 for 30 min, with addition of sodium hydroxide as needed. The suspension was centrifuged and the aqueous phase removed and discarded. The solid was resuspended in 2N NaOH solution (1000 g), centrifuged a second time and then re-suspended in water (2×1000 g, water phase pH 7). The solid product was dried at 45–50° C., under vacuum (for about 4–5 days), to a final water content of <2%, to yield the product as a tan solid.

Yield: 175 g

EXAMPLE 9

4-(4-fluorophenyl)-2-bromo-1-(3-phenylpropyl)-5-(4pyridyl)-imidazole 1,3-Dihydro-1-(3-phenylpropyl)-4-(4-fluorophenyl)-5(4-pyridyl)-2H-imidazol-2-one (100 g, 0.26 mol) was mixed with $POBr_3$ (268.7 g, 0.93 mol) and sulfolane (200 g) and the reaction mixture was heated to a temperature of 120–125° C. for 1–2 h. Upon completion, the reaction mixture was cooled to 40° C. Cautiously, over about 30 min, 2N NaOH solution (53 g) was added. Additional 2N NaOH solution (53 g) was then added at faster rate. The reaction mixture was then cooled to 15–20° C. and 4N NaOH solution (802 g) was added to adjust the solution to pH 7–8. The aqueous phase was extracted with t-butylmethyl ether (3×143 g) and the organic phases combined. To the combined organic phase was added t-butylmethyl ether (107 g). The solution was washed with water (2×150 g), resulting in the precipitation of a solid, which was collected by filtration.

HBr Salt:

A solvent exchange solution of t-butylmethyl ether to ethyl acetate was used for the crystallization of the HBr salt.

The t-butylmethyl ether phase was concentrated to 150 g (about ½ volume), diluted with ethyl acetate (460 g) and concentrated again to 160 g. The resulting oil was dissolved in ethyl acetate (460 g), HBr gas (21 g, 0.26 mol) was introduced and the solution heated to reflux, resulting in a separate yellow oil layer. Methanol (80 g) was added to the boiling mixture (65° C.), resulting in formation of a solid. The solution was stirred and cooled to 20–25° C. over about 4 h. The mixture was stirred overnight and cooled to 5° C. Ethyl acetate (160 g) was then added to the solution. The resulting precipitate was suction filtered and washed with ethyl acetate (10 g) to yield the crude product as a yellow solid.

Isolation and Crystallization of the Free Base:

The crude product (63 g) was dissolved in ethyl acetate (567 g) and mixed with saturated $NaHCO_3$ solution (126 g). The mixture was stirred at 18–25° C. for about 2 h, until no further gas evolution was ascertainable. The aqueous phase was maintained at pH 8–9 with the addition of more saturated $NaHCO_3$ solution, as needed. The phases were separated and the organic phase was concentrated to about ⅓ volume. The resulting oil was dissolved in ethyl acetate (100 g) and concentrated to dryness. The oil was suspended in acetone (95 g) and heated at reflux (56° C. ±2° C.) for 1 h. The mixture was cooled over 3 h to 36–30° C., held at this temperature for 2 h, cooled to −10° C. and held at this temperature for 2 h. The resulting solid was vacuum filtered and washed with t-butylmethyl ether (10 g). The mother liquor was concentrated, mixed with acetone (41 g), heated to reflux and cooled according to the above procedure to yield a second crop of product. The solid products from both crops were dried for 1–2 h at 40 deg/50 mbar to yield the product as a tan solid.

Yield: 34 g (30–32%)

EXAMPLE 10

4-(4-fluorophenyl)-2-(4-hydroxy-1-butinyl)-1-(3phenylpropyl)-5-(4-pyridyl)-imidazole 4-(4-Fluorophenyl)-2-bromo-1-(3-phenylpropyl)-5-(4-pyridyl)-imidazole (30.19 g) was mixed with diisopropylamine (100.56 g). To the reaction mixture was added 3-butyn-1-ol (5.304 g), dropwise using a syringe. Diisopropylamine (1.810 g) was then added to the reaction mixture to wash the syringe, followed by addition of triphenylphosphine (1.805 g), Pd(OAc)$_2$ (0.722 g), iron powder (0.384 g), and diisopropylamine (78.64 g). The flask was briefly blanketed with nitrogen, then warmed to 70° C., and maintained at this temperature for 3 h.

The above experiment was repeated several times. If the conversion was determined to be less than 95% after three hours, additional triphenylphosphine (1.805 g) and palladium acetate (Pd(OAc)$_2$) (0.772 g) were added and the temperature maintained until conversion of >95% was achieved.

Upon completion, the reaction mixture was filtered to collect the solid residue. The filtered residue was suspended with ethyl acetate (212.17 g) at 40–50° C., filtered and solvent evaporated to dryness. The resulting oil was dissolved completely in the first filtrate at 70° C. Water (148.608 g) was added to the hot solution and the phases were separated. The organic phase was washed twice with water (148.608 g) at 70° C. The phases were separated again and the organic phase washed with brine (148.608 g) and extracted with 1N HCl (2×146 g). The combined HCl phases were re-extracted with ethyl acetate (99.07 g). The water phase was separated. To the water phase was added 25% ammonia (26.948 g) dropwise, with cooling to 5–10° C. and at a pH 9–10, resulting in formation of a solid. The suspension was stirred for about 45 min and the precipitate collected by filtration. The precipitate was slurried with water (2×148.61 g) and then dried for 16 h at 40° C./50 mbar. The solid was dissolved in a mixture of ethyl acetate (412.21 g) and methanol (35.270 g), and mixed with Deloxan® (5.00 g). The solution was stirred for 24 h at 18–23° C. and filtered. The filtered residue was washed with ethyl acetate (2×15.34 g). The combined mother liquors and washes were rotoevaporated to dryness. The residue was dissolved in a mixture of THF (7.94 g) and toluene (16.0 g) at 70–75° C., cooled slowly over about 2 h to 18–23° C., resulting in formation of a suspension. Toluene (9.2 g) was then added to the suspension. The suspension solids were suction filtered, washed with toluene (3×1.40 g), and then washed with hexane (3×2.02 g). The residue was dried for 16 h at 50° C./50 mbar to yield the product as an off white yellow solid.

Yield: 20.5 g (70.5%)

The above experiment was repeated several times. Recrystallization of the above residue as described yielded Form B of the product. Recrystallization of the above residue from acetonitrile, yielded Form A of the product.

EXAMPLE 11

N-(3-phenylpropyl)-N'-[(2,2-dimethoxy-2-(4-pyridyl)-1-(4-flyuorophenyl)ethyl)] urea To a solution of 2,2-dimethoxy-2-(4-pyridyl)-1-(4-fluorophenyl)ethanamine (1.22 g, 4.4 mmol) in THF (10 mL) was added a solution of (3-isocyanatopropyl)-benzene (1.61 g, 10 mmol) in THF (10 mL). The resulting mixture was stirred at room temperature for 30 minutes. The reaction was quenched by addition of water (50 mL) and extracted with ethyl acetate (2×50 mL). The combined ethyl acetate extract was washed with water (50 mL), brine (50 mL) and dried with Na$_2$SO$_4$. After removal of solvent, the crude product was purified by column chromatography to yield the product as a light brown solid.

Yield: 0.83 g (43%) m.p. 162.5–165.5° C.

EXAMPLE 12

Synthesis of 4-(4-fluorophenyl)-2-bromo-1-(3-phenylpropyl)-5-(4-pyridyl)-imidazole A reaction vessel was charged with POCl$_3$ (1500.0 g, 9.78 mol). Br$_2$ (184.9 g, 1.157 mol) was then added in one portion at ambient temperature. The reaction mixture was cooled to 10° C. and then PBr$_3$ (313.0 g, 1,157 mol) was added over 25 min. under vigorous stirring. The temperature of the reaction mixture increased to 20° C. After addition, stirring was continued for another 1.5 h, maintaining the temperature in the range of 10–20° C. The formed PBr$_5$ precipitated as a yellow solid. The reaction mixture was warmed to 25° C. and 1,3-dihydro-1-(3-phenylpropyl)-4-(4-fluorophenyl)-5-(4-pyridyl)-imidazol-2-one (150.0 g 0,386 mol) was added in one portion. After addition, the reaction mixture was heated to about 30° C. and stirring was continued for 24 h. The suspension changed to a dark solution. The POCl$_3$ was distilled off under vacuum at a temperature below 35° C., to yield a viscous oil. This oil was added to a mixture of ethyl acetate (1000 g) and aqueous ammonia (25 w %, 1000 g) over about 1.25 hours, with cooling. The resulting two phases were separated, the aqueous phase was extracted with ethyl acetate (500 g) and the combined organic phases were washed with water (200 g) at 70° C. The organic phase was concentrated to approximately 30% of the original volume. To the warmed reaction mixture, was then added triethylamine (600 g) and an additional amount of the solvent (about 150 g) was removed in vacuo, resulting in the crystallization of the desired product. The reaction mixture was cooled to 0° C. and stirred for 12 h. The product was filtered off, washed with triethylamine (50 g) and dried at 40° C. under vacuum, to yield the crude product.

The mother liquor was concentrated to an oil. To the oil was then added acetone (25 g), resulting in precipitation of the desired product. The precipitate was filtered off, washed with acetone (7 g), then with methyl tert-butylether (8 g) and dried at 40° C. under vacuum to yield a second crop of the crude product.

Both crops of the isolated product were slurried in a mixture of triethylamine (10 g) and acetone (100 g), under reflux for 30 min, then cooled to 25° C. and stirred overnight. The precipitate was filtered off, washed with triethylamine (25 g), then with acetone (10 g) and dried at 40° C. under vacuum to yield the title compound.

HPLC purity: 99%

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for preparing a compound of formula (I)

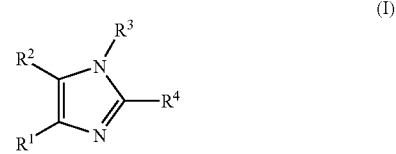

wherein
R¹ is selected from the group consisting of phenyl, substituted phenyl, (where the substituents are selected from $C_1-C_5$alkyl, halogen or trifluoromethyl);
R² is a saturated or unsaturated 6 membered ring with 5 carbon atoms and one nitrogen atom;
R³ is carbocyclic aryl$C_1-C_5$alkyl, wherein the aryl group is optionally substituted with substituents selected from $C_1-C_5$alkyl, $C_1-C_5$alkoxy, halogen, amino, $C_1-C_5$alkylamino or di($C_1-C_5$alkyl) amino);
R⁴ is

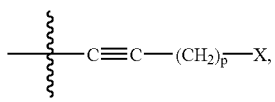

where
p is an integer from 0 to 9;
X is selected from the group consisting of hydrogen, hydroxy, vinyl, substituted vinyl, (where one or more substituents are selected from fluorine or chlorine), ethynyl, substituted ethynyl (where the substituent is selected from fluorine or chlorine), $C_1-C_5$alkyl, substituted $C_1-C_5$alkyl (where the alkyl substituents are selected from one or more of $C_1-C_5$alkoxy and trihaloalkyl,), and $C_3-C_7$cycloalkyl and pharmaceutically acceptable salts thereof;
comprising

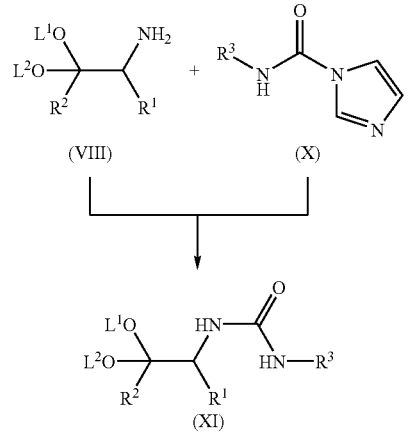

reacting a compound of formula (VIII), wherein L¹ and L² are independently selected from the group consisting of $C_1-C_4$alkyl and $C_1-C_4$aralkyl; or L¹ together with L² is selected from the group consisting of —CH₂—CH₂—(optionally substituted with one to four $C_1-C_3$ alkyl), and —CH₂—CH₂—CH₂—(optionally substituted with one to six $C_1-C_3$ alkyl); with a compound of formula (X), to produce the corresponding compound of formula (XI);

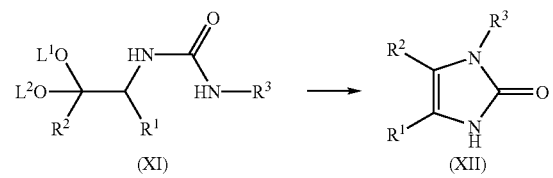

cyclizing the compound of formula (XI), under acid conditions of pH less than about 7, to produce the corresponding compound of formula (XII);

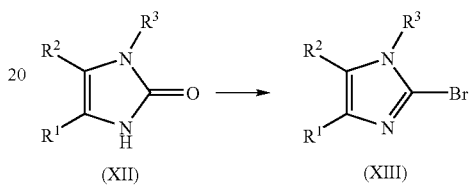

reacting the compound of formula (XII) with POBr₃, PBr₅, or a mixture of PBr₃ and Br₂, to yield the corresponding compound of formula (XIII);

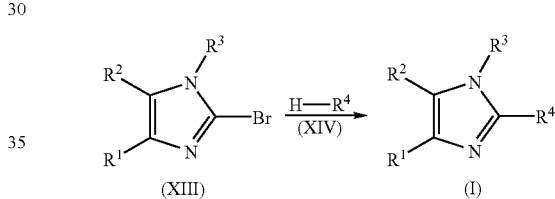

displacing the bromine on the compound of formula (XIII) by reacting with a compound of formula (XIV), to produce the corresponding compound of formula (I).

2. The process of claim 1 wherein R¹ is 4-fluorophenyl, R² is 4-pyridyl, R³ is 3-phenylpropyl and R⁴ is

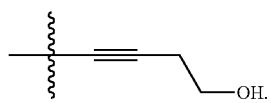

3. The process of claim 1 wherein the compound of formula (XII) is reacted with POBr₃ in tetramethylenesulfone.

* * * * *